United States Patent [19]
Kelley

[11] Patent Number: 5,171,265
[45] Date of Patent: Dec. 15, 1992

[54] SELF-LUBRICATING OCULAR PROSTHESIS

[76] Inventor: Kevin V. Kelley, 63 Bradford Way, Voorhees, N.J. 08043

[21] Appl. No.: 892,980

[22] Filed: Jun. 3, 1992

[51] Int. Cl.$^5$ ............................................. A61F 2/14
[52] U.S. Cl. ....................................... 623/4; 623/901; 264/222; 264/223; 264/DIG. 30
[58] Field of Search ...................... 623/4, 901; 264/2.5, 264/2.7, 222, 223, DIG. 30

[56] References Cited

U.S. PATENT DOCUMENTS

| | | | |
|---|---|---|---|
| 2,467,401 | 4/1949 | Murphey et al. | 623/4 |
| 3,364,501 | 1/1968 | Stafford | 623/4 |
| 3,480,971 | 12/1969 | Smith | 623/4 |
| 4,902,292 | 2/1990 | Joesph | 623/4 |

FOREIGN PATENT DOCUMENTS 2203048 10/1988 United Kingdom .

OTHER PUBLICATIONS

The Making of a Hollow Prosthetic Eye Journal of American Society of Ocularist 1986, 3 pages.
Artificial Eyes and Tear Measurements–Allen et al–American Academy of Ophthalmology pp. 155-157 vol. 87, No. 2, Feb. 1980.
The Anothalmic Socket and the Prosthetic Eye—Vasquez et al Opthalmic Plastic & Reconstructive Surgery pp. 277-280 vol. 5, No. 4, 1989.
Natural Movement for Artificial Eyes-Integrated Orbital Implants, Inc (Pamphlet) 2 pages.
A Dictionary of Terms for the Ocularist-Kelley et al Jun. 1, 1974 pp. 10, 11, 12 and 16.
Bio Coat TM Opt—BioCoat. Products, 2 pages.

*Primary Examiner*—Ronald Frinks
*Attorney, Agent, or Firm*—Thomas A. Lennox

[57] ABSTRACT

A self-lubricating ocular prosthesis includes a solid rigid prosthetic eye body with a chamber in the body opening through an access passage through the posterior surface of the body closed with a releasable cap having an outside face conforming to the posterior surface of the body which abuts the orbital cavity. The cap is of a semi-rigid or flexible polymeric resin to retain a fluid in the chamber which is dispensed through bore openings from the chamber through the surface of the eye body. Liquid may be inserted directly into the cavity through the bore opening while the prosthesis is in place. The prosthesis may also include a dispensing ball or depressible button to dispense fluid from the prosthesis.

22 Claims, 5 Drawing Sheets

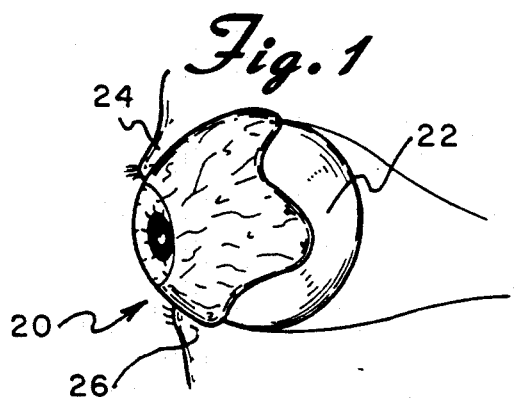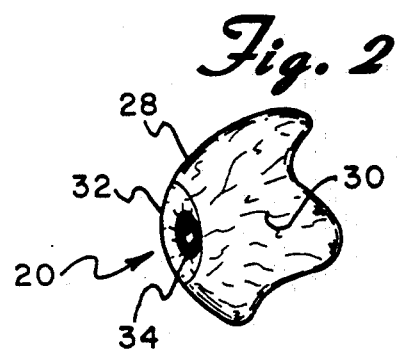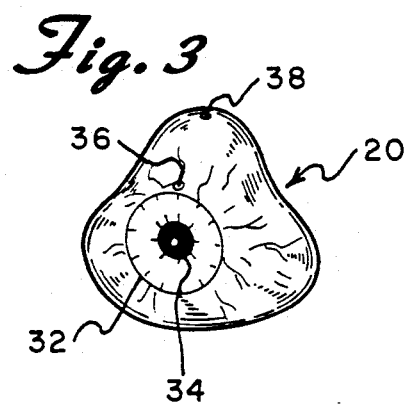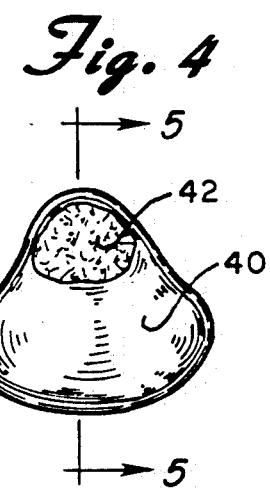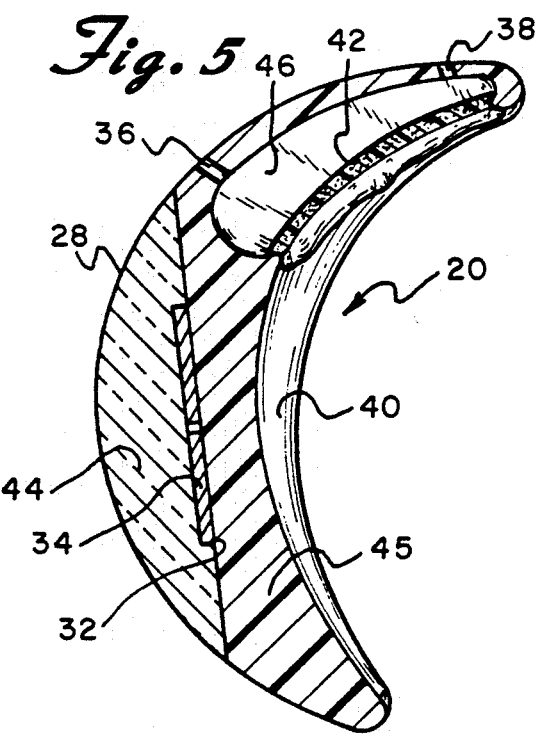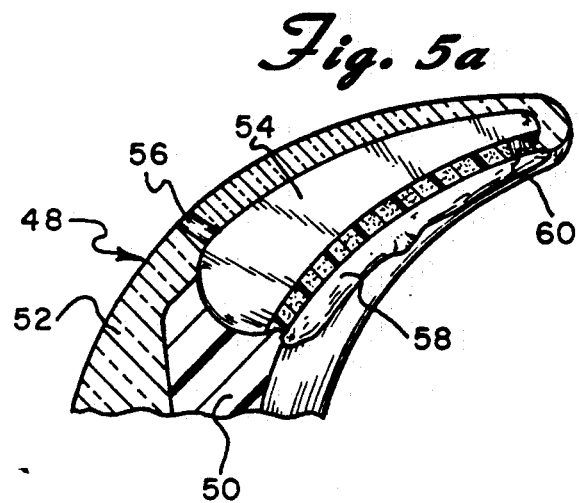

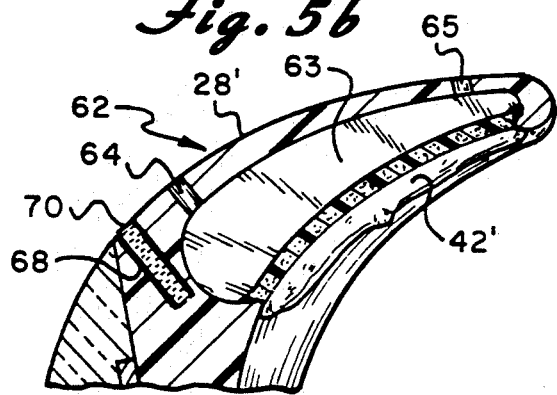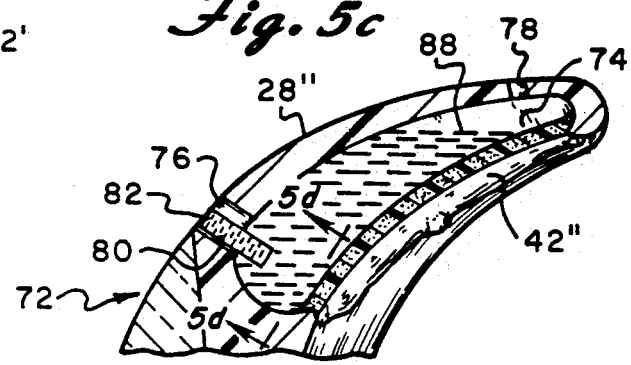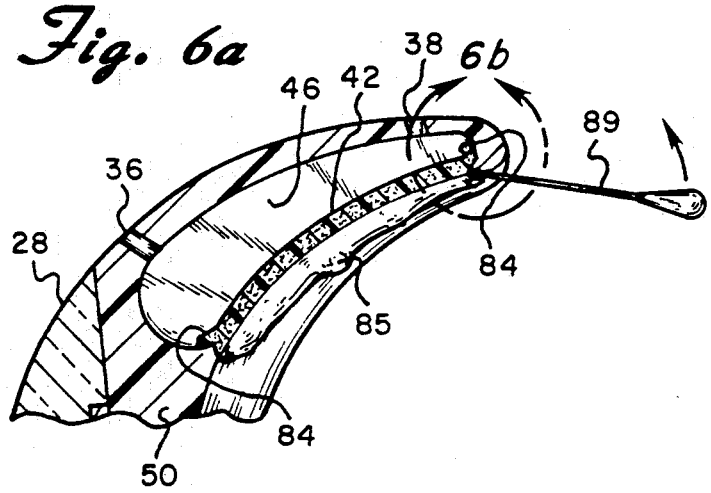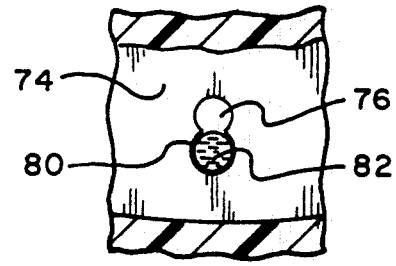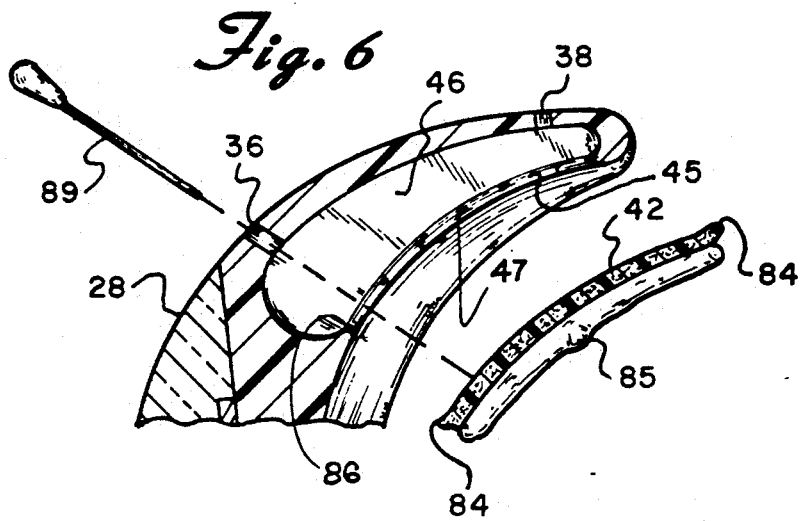

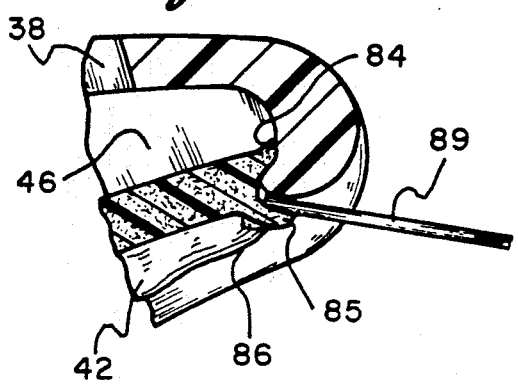
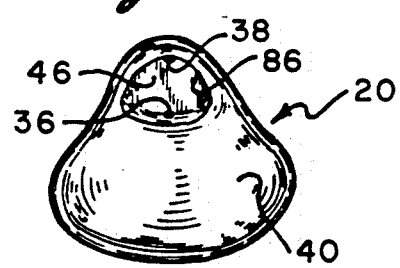
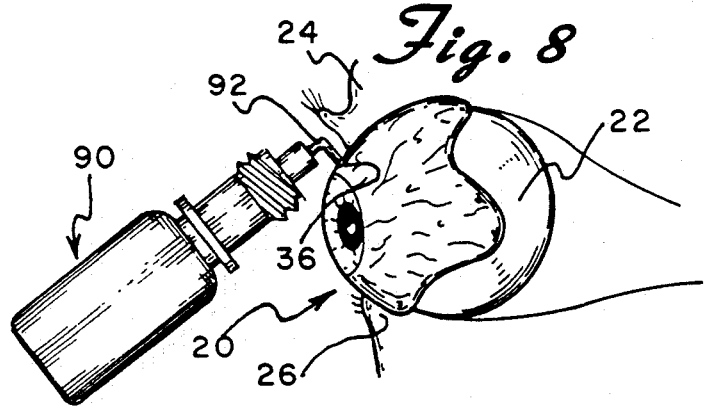
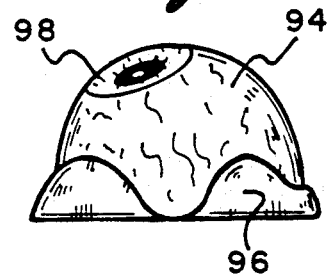
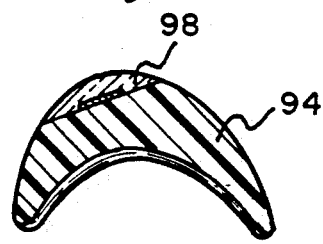
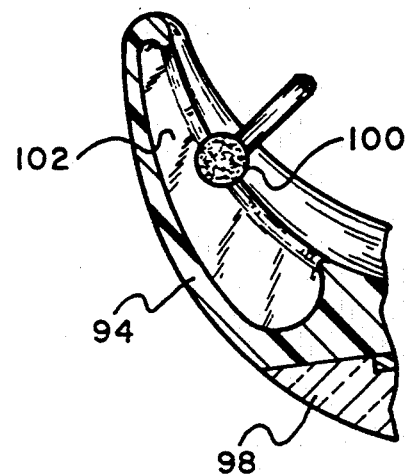

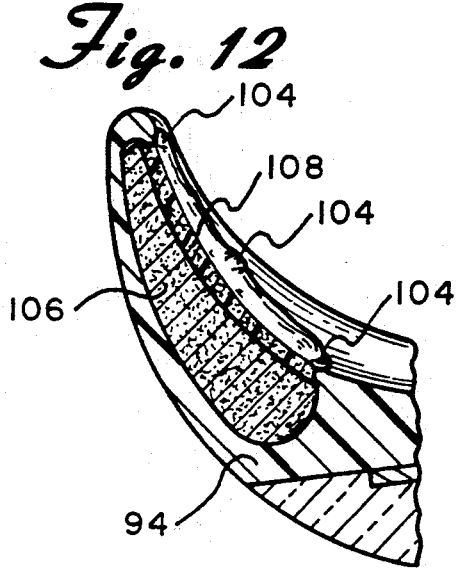
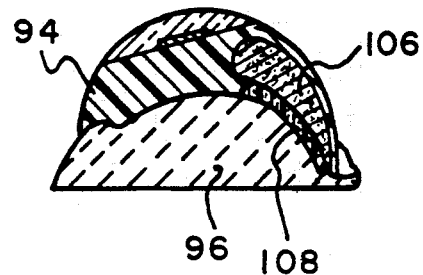
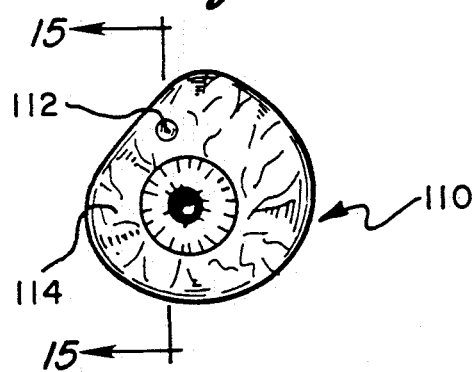
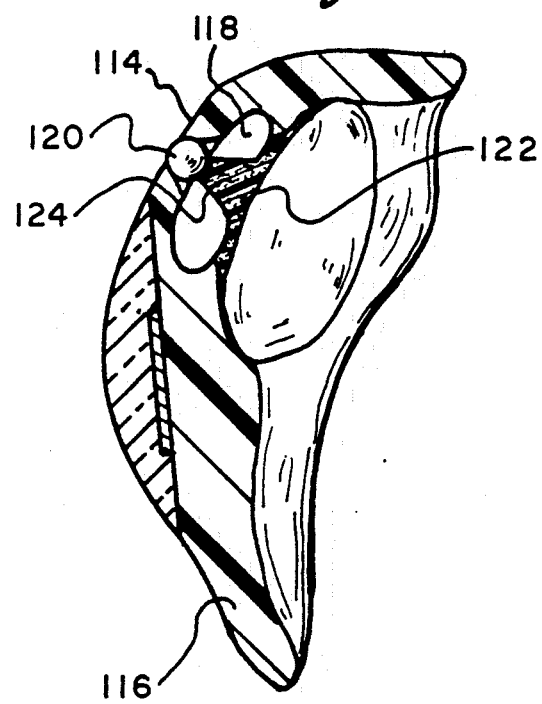
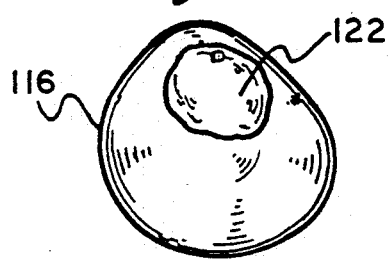

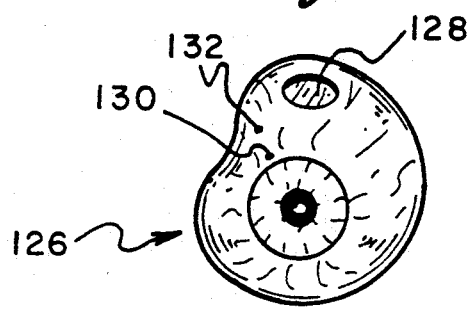
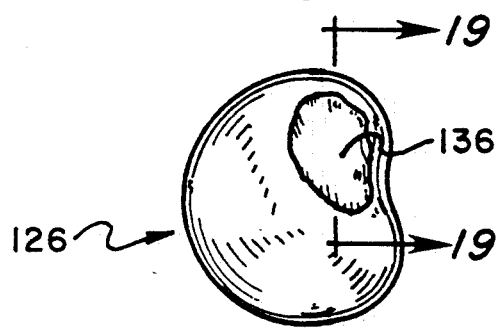
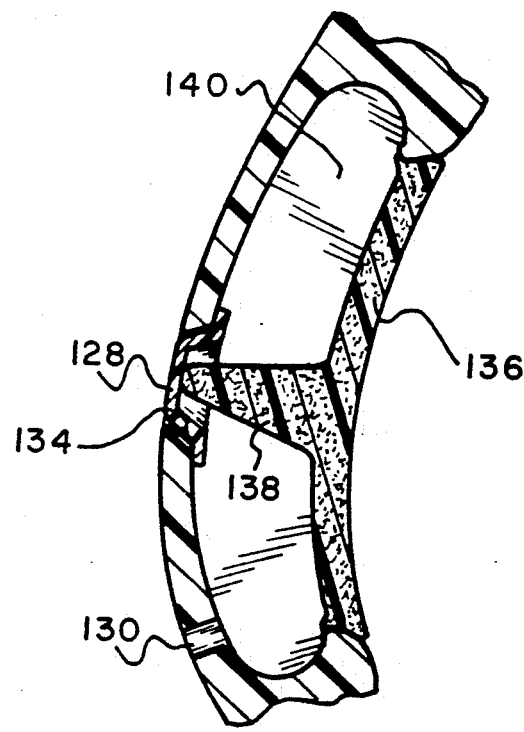

SELF-LUBRICATING OCULAR PROSTHESIS

BACKGROUND OF THE INVENTION

This invention involves a self-lubricating ocular prosthesis and more particularly a prosthetic eye that is a source of lubricant and bactericide coupled with the method of use and method of manufacture of the prosthetic device.

For the person who has lost an eye due to injury, disease, or genetic defect, the art of the Ocularist has long been available to supply an ocular prosthesis including a prosthetic eye that almost exactly matches the person's natural eye. The ocular prosthesis may be necessary following an enucleation, an evisceration or the absence of an eye due to a congenital birth defect. In the vast majority of cases, an orbital implant is surgically implanted onto which the prosthetic eye is inserted. The artificial eye is cast from polymerized polymethacrylate resins using techniques well known in the art. An impression is taken of the eye socket from which is prepared a positive mold on which the synthetic eye is cast. A variety of prosthesis and techniques are used to provide movement of the artificial eye in concert with the person's good eye. These include an enucleation implant or an anophthalmic insert. More recently, orbital implants that are sufficiently porous that the patient's blood vessels and tissues grow into the implant allowing a surgical procedure to give artificial eye movement. A post or peg interconnection is provided between artificial eyes and orbital implants so that the eye moves with the orbital implant which follows the good eye.

Hollow prosthetic eyes have been offered since the 1960's and are more recently described in the article THE MAKING OF A HOLLOW PROSTHETIC EYE by Eric A. Jarling, *JOURNAL OF AMERICAN SOCIETY OF OCULARIST*, circa 1986. This hollow prosthesis is only offered for those patients whose anophthalmic cavity is larger and deeper than normal, specifically those patients that were unable to be fitted with an orbital implant at the time of enucleation, or had experienced extrusion of an implant and were unable to have a second implant. For those patients, the ocular prosthesis would be quite large, and thus heavier. In this manufacturing procedure, two halves of the artificial eye are produced with a hollow interior and bonded together to form an integral prosthesis. The interior cavity of this prosthesis is sealed to avoid intrusion of fluids and bacteria.

Even with these advancements, it has been long well established that for many patients, the blinking and tearing mechanisms of the eye socket do not operate at all or are insufficient to allow the patient comfortable use. The problem of eye dryness is reviewed in an article, ARTIFICAL EYES AND TEAR MEASUREMENTS, by Lee Allen, at al a reprint in *OPHTHALMOLOGY*, February 1980, Vol. 87, No. 2 of a presentation at the Eighty-Fourth Annual Meeting of the American Academy of Ophthalmology in November of 1979, the article being incorporated herein by reference thereto. In addition, continuing problems of bacterial infections are suffered by some prosthetic users. These problems are not unlike those associated with wearers of contact lenses, except the problem is more severe. The increased prevalence of bacteria in the conjunctiva of anophthalmic sockets is reported in the article, THE ANOPHTHALMIC SOCKET AND THE PROSTHETIC EYE-A CLINICAL AND BACTERIOLOGIC STUDY, printed in the Anophthalmic Plastic and Reconstructive Surgery Vol. 5, No. 4, pp 277–280, 1989, also incorporated herein by reference. In this study, the patients were instructed to handle their prosthesis as infrequently as possible, but about twenty-five percent admitted to removing their prosthesis at least once each week. The study concluded that this "frequent manipulation" increased the incidence of bacterial flora.

A number of techniques have been directed to the problem of dry artificial eyes including the use of BioCoat OPT supplied by Bio-Metric Systems, Inc. of Eden Prairie, Minn. This coating is a chemically bonded hydrophilic polymer that is applied to the artificial eye. Periodic retreatment of the coating is required. A solid methyl cellulose lubricant, marketed under the trademark LACRISERT ®, by Merk, Sharp and Dohme of West Point, Penn., has been developed and approved for severe natural dry eye problems by the U.S. Food and Drug Administration. This product is a small solid cylindrical body of lubricant that is inserted under the lower eyelid and allowed to slowly dissipate during the day providing a thickened film and lubrication for the natural eye. This product was also tested for use with artificial eye wearers with limited success. Unfortunately, the liquification of the LACRISERT ® insert requires more liquid than is produced in the anophthalmic socket of many of the patients suffering from dry, unlubricated artificial eyes.

In U.S. Pat. No. 3,364,501 to Wilfred F. Stafford, et al, an inflatable orbital implant is provided with a passageway through the artificial eye to provide fluid irrigation offered to control the secretions which arise at the junction of the body tissue with the implant and create problems of infection and extrusion of the implant over varying periods of time. The Stafford procedure allows the insertion of a small tube to force an irrigating liquid through the passageway to the rear of the artificial eye and through a second passageway through the orbital implant.

Therefore, despite the continuing problem of dry eyes and bacterial growth, none of the devices, treatments or substitutes provide an answer to the problem and none of the devices or methods of the prior art attain the objects described hereinbelow.

SUMMARY OF THE INVENTION

It is an object of the present invention to provide a self-lubricating ocular prosthesis that will provide a continuous supply of lubricating and/or medicinal material to the artificial eye surface and the eye socket. The material may be a viscous liquid or a gelatinous form that is dispensed into the eye socket.

An important object of the present invention is to provide a continuous supply of lubrication allowing for longer intervals between removal of the artificial eye for cleaning of surface deposits on the prosthesis.

It is a further object of the present invention to provide a prosthetic eye that includes a chamber for a supply of material which is dispensed to the eye socket upon demand or by natural movements.

It is an additional object of the present invention to provide a prosthetic eye that provides a continuous supply of liquid which is sufficient to liquify the LACRISERT ® lubricant whether it is inserted under the eyelid or in a receptacle in the prosthetic eye.

It is a specific object of the present invention to provide a prosthetic eye that has a reservoir of lubricating or medicinal material with a mechanism that allows the natural eye movement to discharge liquid from the eye.

It is an additional specific object of the present invention to provide a prosthetic eye with a reservoir connected to a push button on the eye surface to dispense liquid or gel as needed by the wearer.

A particular object of the present invention is to provide a prosthetic eye that can provide a continuous discharge or a discharge upon demand of a suitable bactericide or bacterial retarder to essentially eliminate the problem of bacterial infections in ocular prosthesis wearers.

It is a further object of the present invention to provide an artificial eye with a more "wet" looking anterior surface for cosmetic purposes.

It is a particular object of the present invention to provide a self-lubricating artificial eye with a chamber that is easily cleaned by the wearer.

It is an additional object of the invention to provide a self-lubricating prosthesis that is light in weight and exerts less pressure on the lower eyelid of the wearer.

It is an object of the present invention to provide a self-lubricating artificial eye prosthesis that includes a chamber that can be filled with lubricant or medicine with an applicator without removal of the prosthesis.

It is a further object of the present invention to provide a self-lubricating ocular prosthesis with at least one chamber for storing lubricant that can be viewed by the wearer to determine how much of the lubricant has been used.

An aspect of the invention is a self-lubricating ocular prosthesis for use in a person's orbital cavity. The prosthesis includes a solid rigid prosthetic eye body that includes an anterior convex surface through which an iris-cornea-sclera simulation is visible and a posterior surface, proximately conforming to a surface of the person's orbital cavity. The prosthesis further includes a first chamber in the body defining a reservoir volume and an access passage from the first chamber through the posterior surface of the body. The prosthesis also includes a cap releasably closing the access passage and the cap includes an outside face proximately conforming to the posterior surface of the body, and a composition of polymeric material chosen from the group consisting of semi-rigid and flexible polymeric resins. The prosthesis further includes a bore opening from the first chamber through a surface of the body.

It is preferred that the bore opening from the first chamber be through the anterior surface of the body. It is further preferred that the bore opening be a round hole of a diameter in the range of about one-half to about two millimeters. It is also preferred that the access passage and the cap include a plurality of annular detents holding the cap in place closing the access passage. It is further preferred that the ocular prosthesis further includes a vent hole opening from the first chamber to a surface of the prosthetic eye. It is also preferred that the vent hole open from the first chamber to the posterior surface. It is more preferred that the vent hole open through the cap to the posterior surface. It is also preferred that the ocular prosthesis further include dispensing means in the prosthetic eye to discharge material from the first chamber to the orbital cavity. It is further preferred that the dispensing means includes a circular opening from the first chamber to the anterior surface, a sphere of a diameter larger than the circular opening but small enough that a portion of the sphere can extend out through the circular opening while allowing the sphere to freely rotate and allow material in the first chamber to flow out of the circular opening. It is also preferred that the dispensing means include an aperture through the anterior surface of the body in communication with the first chamber and a membrane member proximate the anterior surface closing the aperture. It is further preferred that the dispensing means include an aperture from the first chamber to the anterior surface, a button of a shape less that the shape of the aperture but small enough that a portion of the button can extend out through the aperture, and means to bias the button against the circular opening while allowing the button to be pushed into the first chamber to urge material in the first chamber to flow out of the bore opening. It is also preferred that the cap be of a composition chosen from the group consisting of silicone rubber and light cured acrylic resin. It is further preferred that the ocular prosthesis further include a second chamber and a second bore opening from the second chamber to the anterior surface. It is also preferred that the second bore opening be positioned immediately below the first bore opening. It is further preferred that the second bore opening to the second chamber abut and communicate directly with the first bore opening. It is also preferred that the second chamber open to the first chamber.

Another aspect of the invention is a method of using a self-lubricating ocular prosthesis in a person's orbital cavity. The method includes providing an ocular prosthesis as described above and inserting the prosthetic eye body into the person's orbital cavity. The method continues by injecting a material chosen from the group consisting of a liquid and a gel into the chamber through the bore opening, and applying finger pressure to the anterior surface of the body to eject material from the bore opening as needed. Another aspect of the invention is another method of using a self-lubricating ocular prosthesis in a person's orbital cavity, the method includes providing an ocular prosthesis as described above that includes a dispensing means in the prosthetic eye to discharge material from the first chamber to the orbital cavity. After inserting the prosthetic eye body into the person's orbital cavity and injecting a material chosen from the group consisting of a liquid and a gel into the chamber through the bore opening, the method continues by actuating the dispensing means to eject material from the chamber into the orbital cavity. It is preferred that the material be a viscous or gelatinous eye lubricant, and more preferred that the fluid include a medicine.

Yet another aspect of the invention is a method of producing a self-lubricating ocular prosthesis for use in a person's orbital socket. The method includes preparing a positive mold with a surface proximating the person's eye socket and casting a solid prosthetic eye body which includes an anterior convex surface through which an iris-cornea sclera simulation is visible, and a posterior surface conforming to the surface of the positive mold. The method continues by excavating a first chamber in the body defining a reservoir volume through an access passage through the posterior surface of the body. The method then continues by filling the first chamber with filler means to temporarily fill the void and be easily removable and applying a release agent to surface of the access passage, the posterior surface, and the surface of the positive mold. The method then continues by filling the access passage with polymeric material chosen from the group consisting of uncured semi-rigid and flexible polymeric resins and partially cured semi-rigid and flexible polymeric resins. The method then continues by pressing the posterior surface against the surface of the positive mold and curing the polymeric material to form a cap releasably closing the access passage with an outside face proximately conforming to the posterior surface of the body. The method then continues by removing the cap and removing the filler means, and finally drilling a bore opening through the surface of the body into the first chamber. It is preferred that the method further include providing a lip between the access passage and the chamber and carving a plurality of spaces in the filler means below the lip before filling the access passage with the polymeric material.

BRIEF DESCRIPTION OF THE DRAWINGS

FIG. 1 is a perspective view of a device of the present invention on an orbital implant in a patient's eye socket.

FIG. 2 is a side perspective view of the device illustrated in FIG. 1 removed from the eye socket.

FIG. 3 is a top frontal perspective view of the device.

FIG. 4 is a rear view of the device.

FIG. 5 is a cross-sectional view taken along lines 5—5 of FIG. 4.

FIG. 5a is a partial cross-sectional view of a second embodiment of the invention.

FIG. 5b is a partial cross-sectional view of a third embodiment of the invention.

FIG. 5c is a partial cross-sectional view of a fourth embodiment of the invention.

FIG. 5d is a partial cut away front view of the device illustrated in FIG. 5c.

FIG. 6 is a partial cross-sectional view of the device illustrated in FIG. 5, showing removal of the cap.

FIG. 6a is a second view of FIG. 6 illustrated another way of removal of the cap.

FIG. 6b is an enlarged view of a portion of FIG. 6a.

FIG. 7 is a rear perspective view of the device of FIGS. 1 through 5 with the cap removed to show the internal cavity.

FIG. 8 is a perspective view of the device illustrated in FIG. 1 with a lubricant being added to fill the chamber while the eye is in place.

FIG. 9 is an elevational view of a prior art prosthetic artificial eye resting on a stone mold reproducing the posterior shape of the artificial eye.

FIG. 10 illustrates a cross-sectional view of said artificial eye removed from the mold.

FIG. 11 illustrates a partial cross-sectional view of the eye inverted to grind out a chamber opening to the posterior side.

FIG. 12 is a cross-sectional view of the same eye showing the packing of the cavity with plasticine or wax leaving a depth for the cap and an application of the resin for the cap.

FIG. 13 is a cross-sectional view wherein liquid resin has been added on top of the plasticine or wax and the posterior surface of the artificial eye is pressed against the mold.

FIG. 14 is a frontal view of a fifth embodiment of the invention.

FIG. 15 is a cross-sectional view taken along lines 15—15 of FIG. 14.

FIG. 16 is a rear view of the device of FIG. 14.

FIG. 17 is a frontal perspective view of a sixth embodiment of the invention.

FIG. 18 is a rear view of the device of FIG. 17.

FIG. 19 is a cut-away cross-sectional view taken along lines 19—19 of FIG. 18.

DESCRIPTION OF PREFERRED EMBODIMENTS

Ocular prosthesis 20 in the form of an artificial eye is illustrated in FIG. 1 in place on orbital implant 22 under upper eyelid 24 and lower eyelid 26. In FIG. 2, device 20 has been removed exposing anterior surface 28 through which sclera simulation 30, iris simulation 32 and cornea simulation 34 is visible. The front perspective view of FIG. 3 shows one thirty-second inch round bore opening 36 and one thirty-second inch round vent opening 38 opening through anterior surface 28 above iris simulation 32 barely visible through sclera simulation 30. In these locations both openings are under upper eyelid 24 when in use. In FIG. 4, the rear perspective view shows posterior surface 40 and cap 42. In FIG. 5, transparent center cast section 44 covers and provides the visual appearance to display iris simulation 32 and cornea simulation 34 on the main body of the acrylic casting body 45. As also shown in FIG. 6 cavity 46 opens through access 47 to posterior surface 40 and through openings 36 and 38 through anterior surface 28. Cap 42 releasably closes cavity 46 and conforms to posterior surface shape 40. Alternative embodiments are illustrated in FIGS. 5a, 5b, and 5c. Artificial eye 48 is cast of body resin 50 with clear acrylic resin section 52 essentially covering the entire anterior surface and making cavity 54 visible when the wearer lifts upper eyelid 24 to check the contents of the cavity. Bore opening 56 opens to the anterior surface and vent hole 60 opens directly through cap 58 to the posterior surface. In FIG. 5b, ocular prosthesis 62 includes cavity 63 closed by cap 42'. The "prime" and "double prime" designations throughout the specification indicate that that element is essentially identical to that of an earlier figure. Bore opening 64 and vent opening 65 open from cavity 63 through anterior surface 28'. Cavity 68 is drilled into solid body to receive LACRISERT ® insert 70 into that cavity opening directly through anterior surface 28'. Cavity 68 is positioned directly below bore opening 64 so that lubricant flowing downwardly provides sufficient lubrication for the LACRISERT ®. In FIG. 5c, device 72 includes bore openings 76 and LACRISERT ® bore opening 80 drilled side by side and joined together opening from the cavity through anterior surface 28". Vent hole 78 provides the standard air vent to facilitate flow. In this embodiment, the LACRISERT ® 82 swells and lubricate through direct contact with lubrication fluid 88 inside cavity 74. As shown in FIGS. 6, 6b, and 7 at least one detent projection 84 extends under lip edge 86 of the eye body around opening to cavity 46. Most views show detents, such as detents 84, at each cross-section edge of the cap. However, this is due to choice of the cross-section cut and a plurality of detents are sufficient, preferably about four for each cap, spaced around the periphery. As illustrated in FIG. 6, pin 89 can be used to remove cap 42 either by inserting it through bore opening 36 or vent opening 38 or as shown in FIGS. 6a and 6b by prying under tab 85 of the cap to lift it off. Tab 85 aids in positioning cap 42 over the access opening. In FIG. 7, cap 42 has been removed exposing cavity 46 bounded by lip edge 86. As shown here, bore opening 36 and vent opening 38 open directly from cavity 46 through anterior surface 28. In FIG. 8, standard one half ounce lubricant bottle 90 containing a standard lubricant solution approximating normal tears is equipped with bent polyethylene tube extension 92 which is inserted into hole 36 to fill cavity 46 with the liquid. Since hole 36 is under upper eyelid 24, it is necessary to lift the eyelid to insert tube 92 into the hole and fill the cavity. Through capillary action, the contact with the eyelid draws fluid from the cavity to wet the eye ball.

FIGS. 9 through 13 illustrate a method of manufacture of a device of the present invention. Artificial eye 94 is made using standard methods well known in the art that has been impression fitted to the patient. Clear section 98 is cast in the eye to provide the iris and cornea simulations. Using a prosthesis mix quick set stone or plaster, platform 96 is made for pressing and fabrication of the chamber cap. The stone platform is trimmed and artificial eye 94 is removed as shown in FIG. 10. In FIG. 11, the artificial eye is inverted so that the posterior surface is facing upwardly. Using rotary ball grinder 100, cavity 102 is routed out of the eye from the rear. In FIG. 12 plasticine, wax, clay, or Silly Putty ® are used as filler plug 106 in the cavity to form the space that will remain open. A plurality of detents 104, similar to detents 84 above, are formed by forming a plurality of small hollows under the lip after which medical grade R.T.V. silicone, such as Dow Corning R.T.V. No. 382 silicone is spread over the plug. Platform 96 is re-engaged and pressed for about one minute against the posterior surface of eye 94 forming silicone resin cap 108 to the exact shape of platform 96. When the silicone rubber has fully cured, platform 96 is removed, the cap is pried off and the putty removed. Holes are drilled into the cavity at the chosen points. Twist drills, size sixty through eighty are used to drill the holes into the body, that is the bore openings and vent openings into the chambers. For certain embodiments, the cap may be shaped to hold a ball or button in place by merely indenting the putty to the chosen shape and allowing the silicone rubber to flow into the cavity and upon curing to form the means to hold the ball or button in place. The chamber may be positioned at any location in the artificial eye, but it is preferred that the chamber be positioned at the top upper most section so that the bore opening can be under the upper eyelid. The liquid flows outwardly under the lid and over the prosthesis and down to reach the lower portions of the eye. The chamber is ground with a small ball burr with an undercut leaving a rim around the circumference of the chamber rim to provide a surface for detents extending from the cap to hold the cap in place. The interior of the chamber is polished. The R.T.V. silicone is catalyzed for gelling in about twenty seconds. The chamber is overfilled and immediately the posterior surface of the artificial eye is pressed against the stone platform mold covered with a thin film of Vaseline ®. Hard hand pressure is applied for at least one minute to force the silicone into and around the chamber hole. The silicone sets sufficiently in ten minutes or less after which the silicone is lightly polished in the area of the chamber. The silicone is removed from the chamber and trimmed with scissors or a razor blade. The bore opening used to allow the lubricant to weep from the chamber is drilled with a drill or a fine burr and finely polished. Lubricant is placed in the chamber, the cap is placed in position closing the chamber. A notch tab in the chamber access aids in placement of the cap. After the prosthesis has been cleaned and any excess lubricant removed, the prosthesis is inserted into the eye socket and attached to the orbital implant. An alternative cap composition is TRIAD II light cured acrylic resin supplied by Dentsply of York, Pennsylvania. This semi-rigid material is used in the same fashion as the silicone rubber except that it is covered by a transparent film and cured by exposure to the light after which it is trimmed and ground to the proper shape and surface smoothness.

While devices with only one large chamber and a small chamber are illustrated, it will be clear that a plurality of chambers of the same or different sizes may be provided in the artificial eye. These chambers may be charged with the same lubricant or may be charged with different materials. Thus one chamber can be filled with a lubricant, while the other can be charged with a medicine, such as a bactericide, antihistamine or the like.

Certain devices and mechanisms in the artificial eye are described hereinbelow to aid in dispensing the lubricant from the artificial eye. The simplest method is merely to have the patient press on the prosthesis thus exerting pressure on the cap against the orbital implant. This tends to dispense a small amount of lubricant from the chamber through the weep hole and effectively lubricate the eye. The flexible or semi-rigid character of the cap material allows the cap to flex when pressure is applied to dispense liquid from the chambers.

In FIG. 14, device 110 utilizes ball applicator 112 which rotates freely while protruding through anterior surface 114. As shown in FIG. 15, chamber 118 is carved out of body 116. Ball 120 is slightly larger than the diameter of the hole extending through anterior surface 114 from the chamber. Cap 122 is formed of silicone rubber with extension 124 extending into the space of chamber 118 and holding ball 120 against the hole while allowing it to rotate as it contacts the upper eyelid. Another applicator device is illustrated in FIGS. 17 through 19 wherein device 126 include button 128 flush with the anterior surface proximate weep hole 130 and vent hole 132, all the openings extending into chamber 140. Button 128 is molded of the TRIAD II light cured acrylic resin and is shaped to extend out through opening 134 but of a size too large to come out of the hole. Cap 136 is formed with extension 138 to abut the rear surface of button 128 and hold it in position. When button 128 is depressed with the person's finger, lubricant is expelled through weep hole 130.

While this invention has been described with reference to the specific embodiments disclosed herein, it is not confined to the details set forth and the patent is intended to include modifications and changes which may come within and extend from the following claims.

I claim:

1. A self lubricating ocular prosthesis for use in a person's orbital cavity, the prosthesis comprising:
    (a) a solid rigid prosthetic eye body comprising an anterior convex surface through which an iris-cornea-sclera simulation is visible and a posterior surface, proximately conforming to a surface of the person's orbital cavity,
    (b) a first chamber in the body defining a reservior volume,
    (c) an access passage from the first chamber through the posterior surface of the body,
    (d) a cap releasably closing the access passage, the cap comprising:

(i) an outside face proximately conforming to the posterior surface of the body, and
(ii) a composition of polymeric material chosen from the group consisting of semirigid and flexible polymeric resins, and
(e) a bore opening from the first chamber through a surface of the body.

2. The ocular prosthesis of claim 1 wherein the bore opening from the first chamber is through the anterior surface of the body.

3. The ocular prosthesis of claim 1 wherein the bore opening is a round hole of a diameter in the range of about one-half to about two millimeters.

4. The ocular prosthesis of claim 1 wherein the access passage and the cap comprise a plurality of annular detents holding the cap in place closing the access passage.

5. The ocular prosthesis of claim 1 further comprising a vent hole opening from the first chamber to a surface of the prosthetic eye.

6. The ocular prosthesis of claim 5 wherein the vent hole opens from the first chamber to the posterior surface.

7. The ocular prosthesis of claim 6 wherein the vent hole opens through the cap to the posterior surface.

8. The ocular prosthesis of claim 1 further comprising dispensing means in the prosthetic eye to discharge material from the first chamber to the orbital cavity.

9. The ocular prosthesis of claim 8 wherein the dispensing means comprises:
(a) a circular opening from the first chamber to the anterior surface,
(b) a sphere of a diameter larger than the circular opening but small enough that a portion of the sphere can extend out through the circular opening, and
(c) means to hold the sphere against the circular opening while allowing the sphere to freely rotate and allow material in the first chamber to flow out of the circular opening.

10. The ocular prosthesis of claim 8 wherein the dispensing means comprises an aperture through the anterior surface of the body in communication with the first chamber and a membrane member proximate the anterior surface closing the aperture.

11. The ocular prosthesis of claim 8 wherein the dispensing means comprises:
(a) an aperture from the first chamber to the anterior surface,
(b) a member comprising:
(i) a surface of a shape that will not fit through the aperture, and
(ii) an integral button raised from the surface of the member of a size and shape sufficient to extend through the aperture and position a top surface of the button flush with the anterior surface of the eye body, and
(c) means to bias the button against the circular opening while allowing the button to be pushed into the first chamber to urge material in the first chamber to flow out of the bore opening.

12. The ocular prosthesis of claim 1 wherein the cap is of a composition chosen from the group consisting of silicone rubber and light cured acrylic resin.

13. The ocular prosthesis of claim 1 further comprising a second chamber and a second bore opening from the second chamber to the anterior surface.

14. The ocular prosthesis of claim 13 wherein the second bore opening is positioned immediately below the first bore opening.

15. The ocular prosthesis of claim 13 wherein the second bore opening to the second chamber abuts and communicates directly with the first bore opening.

16. The ocular prosthesis of claim 14 wherein the second chamber opens to the first chamber.

17. A method of using a self lubricating ocular prosthesis in a person's orbital cavity, the method comprising:
(A) providing an ocular prosthesis comprising:
(i) a solid rigid prosthetic eye body comprising an anterior convex surface through which an iris-cornea-sclera simulation is visible and a posterior surface, proximately conforming to a surface of the person's orbital cavity,
(ii) a first chamber in the body defining a reservoir volume,
(iii) an access passage from the first chamber through the posterior surface of the body,
(iv) a cap releasably closing the access passage, the cap comprising:
(a) an outside face proximately conforming to the posterior surface of the body, and
(b) a composition of polymeric material chosen from the group consisting of semirigid and flexible polymeric resins, and
(v) a bore opening from the first chamber through a surface of the body,
(B) inserting the prosthetic eye body into the person's orbital cavity,
(C) injecting a material chosen from the group consisting of a liquid and a gel into the chamber through the bore opening, and
(D) applying finger pressure to the anterior surface of the body to eject material from the bore opening.

18. A method of using a self lubricating ocular prosthesis in a person's orbital cavity, the method comprising:
(A) providing an ocular prosthesis comprising:
(i) a solid rigid prosthetic eye body comprising an anterior convex surface through which an iris-cornea-sclera simulation is visible and a posterior surface, proximately conforming to a surface of the person's orbital cavity,
(ii) a first chamber in the body defining a reservoir volume,
(iii) an access passage from the first chamber through the posterior surface of the body,
(iv) a cap releasably closing the access passage, the cap comprising an outside face proximately conforming to the posterior surface of the body,
(v) a bore opening from the first chamber through a surface of the body, and
(vi) dispensing means in the prosthetic eye to discharge material from the first chamber to the orbital cavity,
(B) inserting the prosthetic eye body into the person's orbital cavity,
(C) injecting a material chosen from the group consisting of a liquid and a gel into the chamber through the bore opening, and
(D) causing the dispensing means to eject material from the chamber into the orbital cavity.

19. The method of claim 18 wherein the fluid is an viscous or gelatinous eye lubricant.

20. The method of claim 19 wherein the fluid comprises a medicine.

21. A method of producing a self lubricating ocular prosthesis for use in a person's orbital socket, the method comprising:
   (a) preparing a positive mold with a surface proximating the person's eye socket,
   (b) casting a solid prosthetic eye body comprising an anterior convex surface through which an iris-cornea-sclera simulation is visible, and a posterior surface conforming to the surface of the positive mold,
   (c) excavating a first chamber in the body defining a reservoir volume through an access passage through the posterior surface of the body,
   (d) filling the first chamber with filler means to temporarily fill the void and be easily removable,
   (e) applying a release agent to surface of the access passage, the posterior surface, and the surface of the positive mold,
   (f) filling the access passage with polymeric material chosen from the group consisting of uncured semirigid and flexible polymeric resins and partially cured semirigid and flexible polymeric resins,
   (g) pressing the posterior surface against the surface of the positive mold,
   (h) curing the polymeric material to form a cap releasably closing the access passage with an outside face proximately conforming to the posterior surface of the body,
   (i) removing the cap and removing the filler means, and
   (j) drilling a bore opening through surface of the body into the first chamber.

22. The method of claim 21 further comprising providing a lip between the access passage and the chamber and carving a plurality of spaces in the filler means below the lip before filling the access passage with the polymeric material.

* * * * *